United States Patent
Wei et al.

(10) Patent No.: US 7,521,568 B2
(45) Date of Patent: Apr. 21, 2009

(54) ENANTIOPURE 4-DEOXYPENTENOSIDES, DIHYDROPYRANS AND TETRAHYDROPYRANS AND SYNTHESES THEREOF

(75) Inventors: Alexander Wei, West Lafayette, IN (US); Fabien P. Boulineau, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1031 days.

(21) Appl. No.: 10/319,335

(22) Filed: Dec. 13, 2002

(65) Prior Publication Data

US 2003/0181402 A1    Sep. 25, 2003

Related U.S. Application Data (60) Provisional application No. 60/340,302, filed on Dec. 14, 2001.

(51) Int. Cl.
    *C07D 315/00*    (2006.01)
(52) U.S. Cl. .................. 549/417; 549/419; 549/420; 549/423
(58) Field of Classification Search ................. 549/423, 549/417, 419, 420
    See application file for complete search history.

(56) References Cited

U.S. PATENT DOCUMENTS 5,166,193 A    11/1992    Levin et al.

OTHER PUBLICATIONS

Bartolozzi et al, Organic Letters "A New Procedure for the Preparation of beta-keto-gamma-lactones from Sugars", vol. 2, No. pp. 251-253, (2000).*

Cardona et al, Synlett, "remarkable high-pressure enhancement of enatiopure nitrone cycloadditions to glycals", vol. 12, pp. 14444-1446, (1998).*

Cardona et al, Jol. Org. Chem. vol. 63, No. 21, pp. 7311-7318, "Straightforward Synthesis of Pseudo Aza-C-disaccharides by the Novel Ccloaddition of Enantiopure Cyclic Nitrons to glycals", (1998).*

Alles et al ,'The glucose-specific carrier of the *Escherichia coli* phosphotransferase' Eur. J. Biochem. vol. 269, pp. 4969-4980 (2002).*

Guagnano et al Tetra. Let. vol. 39 pp. 2025-2026 (1998).*

Tolstikov et al, Glycals in enantiospecific synthesis, Russ. Chem. Rev. 62 (6) 579-601 (1993).*

Guthrie et al, A facile synthesis of D-allal and its derivatives, Carbohydrate Research (1979), 72, 285-8, CA 91:491855 Best Availble.*

Tolstikov et al, Benzyl ethers of D- and L-arabinals as chiral synthons in organic synthesis, Synthesis (1988), (3), 221-2, CA 109:149882 Best Availble.*

(Continued)

*Primary Examiner*—Janet L. Andres
*Assistant Examiner*—Raymond Covington
(74) *Attorney, Agent, or Firm*—Henry D. Coleman; R. Neil Sudol; William J. Sapone (57) ABSTRACT

Enantiopure substituted 4-deoxypentenosides (4-DPs) and related dihydropyrans (DHPs) are prepared from common carbohydrates via a novel process. The 4-DPs and related DHPs are amenable to a broad range of stereoselective transformations and are used as synthetic intermediates to prepare a variety of enantiopure tetrahydropyrans (THPs), including rare or exotic sugars and other complex THPs of commercial or medicinal value. In one embodiment of the instant invention, 4-DPs are converted to L-sugars in a novel process that offers distinct advantages over known synthetic methods.

24 Claims, 1 Drawing Sheet

OTHER PUBLICATIONS

Chen et al, Synthesis, conformational analysis, and the glycosidic coupling reaction of substituted 2,7-dioxabicyclo[4.1.0]heptanes: 1,2-anhydro-3,4-di-O- benzyl-.beta.-L- and .beta.-D-rhamnopyranoses, Carbohydrate Research (1993) abstract, 240, 107-17, CA 119:49746 Best Availble.*

Yang et al, Synthesis and glycosidic coupling reaction of substituted 2,7-dioxabicyclo[4.1.0]heptanes: 1,2-anhydro-3,4-di-O-benzyl-.beta.-D-lyxo- and -.alpha.-L-ribopyranose, Carbohydrate Letters (1994), 1(2), 137-141, CA 125:87025 Best Availble.*

Flaherty et al, Hydride addition to 1,2-anhydro sugars: a highly stereoselective route to anhydro alditols, Tetrahedron Letters (1996), 37(7), 961-4.*

Wittman et al. "A Route to Glycals in the Allal and Gulal Series: Synthesis of the Thiosugar of Esperamicin A1" J. Org. Chem. 1990, 55, 1979-1981.

Giese et al. "Diastereoselective Synthesis of Branched 2-Deoxy Sugars Via Radical C-C Bond Formation Reactions" Tetrahedron Letters, 1984, 25, 2743-2746.

Bosman et al. "Oxidation of Diphenyl Diselenide with Ceric Ammonium Nitrate: a Novel Route for Functionalization of Olefins" Tetrahedron Letters 1994, 35, 6525-6528.

De Mico et al. "Radical Additions to Olefins in the Presence of Iodobenzenediacetate: an Easy Route to Alkyl Dithiocyanates" Tetrahedron Letters 1996, 37, 1889-1892.

Poirier et al. "Reaction des Vinylogues d'Hemiacetals et de Leurs Equivalents Synthetiques sur les Ethers d'Enols Heterocycliques" Tetrahedron Letters 1987, 28, 3337-3340.

Crimmins et al. "Asymmetric Total Synthesis of Spongistatins 1 and 2" J. Am. Chem. Soc. 2002, 124, 5661-5663.

Hoffmann et al. "One-Pot Preparation of α-Cyanovinyl Ethers (2-Alkoxy-2-alkenenitriles) from Vinyl Ethers: Elaboration to 3-Alkox-2-oxo-3-alkenenitriles and Aluminum Chloride-Catalyzed Cycloadditions to Cyclopentadiene" Synthesis 1986, 548-551.

Czollner et al. "63.Synthese eines 1,2-trans-konfigurierten, aquatorialen Glycosyl-phosphonat-Analogen von D-myo-Inositol-1,4,5-trisphosphat" Helvetica Chimica Acta 1993, 76, 1013-1025.

Diksic et al. "Synthesis of 2-Deoxy-2-Fluorohexoses by Fluorination of Glycals in Aqueous Media" Carbohydrate Research 1986, 153, 17-24.

R. Murali et al. "Synthesis of 1,2-Cyclopropanated Sugars from Glycals" J. Chem. Soc., Chem. Commun., 1995, 217-218.

Li et al. "Glycosyl Transfer to Nitrogen via Cycloaddition" Organic Letters 1999, 1, 111-113.

Dios et al. "Novel Heeterocycloaddition Reaction of Glycals" J. Org. Chem. 1998, 63, 6673-6679.

Yu et al. "Intramolecular Cyclopropanation of Glycals: Studies toward the Synthesis of Canadensolide, Sporothriolide, and Xylobovide" Organic Letters 2001, 3, 2563-2566.

Boulineau et al. "Synthesis of L-Sugars from 4-Deoxypentenosides" Organic Letters 2002, 4, 2281-2283.

Boulineau et al. "Conversion of D-Glucals into L-Glycals and Mirror-Image Carbohydrates" Organic Letters 2004, 6, 119-121.

Rozen et al. "The Chemistry of Methyl Hypofluorite: Its Reactions with Various Unsaturated Centers" J. Org. Chem. 1994, 59, 4281-4284.

Kuroda et al. "An Enantiospecific Synthesis of Monic Acid C" J. Org. Chem 1986, 51, 956-958.

Shelton et al. "Reaction of N-Bromosuccinimide with Dihydropyran" J. Org. Chem. 1958, 23, 1128-1133.

Boulineau, F.P.; Wei, A. "Synthesis of L-Sugars from 4-Deoxypentenosides" Org. Lett. 2002, 4, 2281-83.

Boulineau, F.P.; Wei, A. "Efficient Conversion of D-Glucals into L-Glycals and Mirror-Image Carbohydrates" submitted Aug. 6, 2003 to Angewandte Chemie.

Umezawa, S. "Structures and Syntheses of Aminoglycoside Antibiotics" Adv. Carbohydr. Chem. Biochem. 1974, 30, 111-82.

O'Neill, P.M., et al. "Efficient Preparations of the beta-Glucuronides of Dihydroartemisinin and Structural Confirmation of the Human Glucuronide Metabolite" J. Med. Chem. 2001, 44, 1467-70.

Yoo-, S.-e et al. "A Novel Anti-Ischemic ATP-Sensitive Potassium Channel (Katp) Opener without Vasorelaxation: N-(6-Aminobendzopyranyl)-N-benzyl-N'-cyanoguanidine Analogue" J. Med. Chem. 2001, 44, 4207-15.

Gerlach, U, et al. "Synthesis and Activity of Novel and Selective Iks-Channel Blockers" J. Med. Chem. 2001, 44, 3831-37.

Lee, E. et al. "Synthesis of (+)-Lasonolide A: (−)-Lasonolide A is the Biologically Active Enantiomer" Bioorg. Med. Chem. Lett. 2002, 12, 3519-20.

Maier, C. A.; Wunsch, B.J. "Novel Sigma Receptor Ligands. Part 2. SAR of Spiro [[2]benzofuran-1,4'-piperidines] and Spiro[[2]benzofuran-1,4'-piperidines]with Carbon Substituents in Position 3" J. Med. Chem. 2002, 45, 4923-30.

Duffy, J.L. et al. "Synthesis and Activity of Novel HIV Protease Inhibitors with Improved Potency Against Multiple PI-Resistant Viral Strains" Bioorg. Med. Chem. Lett. 2002, 12, 2423-26.

Shallenberger, R.S.; Acree, T.E.; Lee, C.Y. "Sweet Taste of D and L-Sugars and Amino-acids and the Steric Nature of their Chemoreceptor Site" Nature 1969, 221,555-56.

McNaught, A.D. "Nomenclature of Carbohydrates" Pur. Appl. Chem. 1996, 68, 1919-2008.

Ko, S.Y. et al. "Total Synthesis of the L-Hexoses" Science 1983, 220, 949-51.

Sowden, J.C. et al. "Carbohydrate C-Nitroalcohols: 6-Nitro-6-desoxy-D-sorbitol. A Convenient Source of L-Gulose" J. Am. Chem. Soc. 1945, 67, 1713-15.

Blanc-Muesser, M, et al. "A Simple Synthesis of L-Idose" Synthesis 1977, 568-69.

Pegram, J.J.; et al., "6-Deoxy-6-(dimethylphenylsilyl)-1,2:3,4-di-O-isopropylidene-beta-L-altropyranose: Synthesis via hydrosilation, and reactivity" Carbohydr. Res. 1988, 184, 276-78.

Tostikov, A. G. et al., "Glycals in enantiospecific synthesis" Russ. Chem. Rev. 1993, 62, 579-601.

Philips, K.D.; Zemlicka, J.; Horwitz, J.P. "Unsaturated Sugars I. Decarboxylative Elimination of Methyl 2,3-Di-O-Benzyl-alpha-D-Glucopyranosiduronic Acid to Methyl 2,3-Di-O-Benzyl-4-Deoxy-beta-L-threo-Pent-4-Enopyranoside" Carbohydr. Res. 1973, 30, 281-86.

Fleming, I.; Sanderson, P.E.J. "A One-Pot Conversion of the Phenyldimethylsilyl Group into a Hydroxyl Group" Tetrahedron Lett. 1987, 28, 4229-32.

* cited by examiner

Table 3. Nucleophilic Ring-Opening of β-Epoxide 2

| entry | nucleophile | react cond | product | yield |
|---|---|---|---|---|
| a | $^{13}CH_3MgI$ | A | | 57%[b] |
| b | vinylMgBr | B | | 78%[c] |
| c | allylMgCl | B | | 70%[b] |
| d | 3-butenylMgBr | B | | 52%[b] |
| e | $PhMe_2Si$-CH$_2$MgCl | B | | 80%[b] |
| f | PhMgBr | A | | 69%[c] |
| g | KCN | C | | 68%[b] |
| h | $NaN_3$ | C | | 77%[b] |
| i | 4-MePhSLi | D | | 72%[c] |
| j | $LiAlD_4$ | E | | 69%[c] |

[a] Reaction conditions. (A) 3.5 equiv of Nu, 1.5 equiv of CuI, THF, −10 °C. (B) 3.5 equiv of Nu, 0.1 equiv of CuI, THF, −10 °C. (C) 10−20 equiv of Nu in aq DMF, rt. (D) 9.0 equiv of Nu in THF, 0°C. (E) 5.0 equiv of Nu in Et$_2$O, rt. [b] Mixture of diastereomers = 10:1 L-altro/D-gluco. [c] Isolated yield

FIGURE 1

ENANTIOPURE 4-DEOXYPENTENOSIDES, DIHYDROPYRANS AND TETRAHYDROPYRANS AND SYNTHESES THEREOF

RELATED APPLICATIONS

This application claims priority from U.S. provisional application No. 60/340,302, filed Dec. 14, 2001.

FIELD OF THE INVENTION

Novel enantiopure substituted 4-deoxypentenosides (4-DPs) and related dihydropyrans (DHPs) are prepared from common carbohydrates via a novel process. 4-DPs and DHPs are amenable to a broad range of stereoselective transformations and are used to prepare a wide variety of novel, enantiopure tetrahydropyrans (THPs). Novel 4-DPs and DHPs of the invention may be used as synthetic intermediates toward higher-order or exotic sugars and other complex THPs of commercial or medicinal value. In one embodiment of the instant invention, 4-DPs and DHPs are converted to L-sugars in a novel process that offers distinct advantages over known synthetic methods.

BACKGROUND OF THE INVENTION

Chiral THP rings are ubiquitous substructures in natural and medicinally active products. Examples of the latter include aminoglycoside antibiotics (Umezawa, S. *Adv. Carbohydr. Chem. Biochem.* 1974, 30, 111-82), antimalarial agents (O'Neill, P. M., et al. *J. Med. Chem.* 2001, 44, 1467-70), selective ion-channel blockers for the treatment of heart disease (Yoo, S.-e. et al. *J. Med. Chem.* 2001, 44, 4207-15; Gerlach, U. et al. *J. Med. Chem.* 2001, 44, 3831-37), macrolide antibiotics and antitumor agents (Lee, E. et al. *Bioorg. Med. Chem. Lett.* 2002, 12, 3519-20), antidepressants (Maier, C. A.; Wunsch, B. *J. Med. Chem.* 2002, 45, 4923-30), and HIV protease inhibitors (Duffy, J. L. et al. *Bioorg. Med. Chem. Lett.* 2002, 12, 2423-26). Other applications include noncalorific sweeteners (Shallenberger, R. S.; Acree, T. E.; Lee, C. Y. *Nature* 1969, 221, 555-56. Levin, G. V. U.S. Pat. No. 4,262,032, 1981), pesticides (Levin, G. V.; Zehner, L. R. U.S. Pat. No. 5,166,193, 1992), ligands and auxiliaries for asymmetric synthesis and/or catalysis, ionophores, and optically active materials.

Many enantiopure THPs are carbohydrates or can be derived from carbohydrate precursors. One important consideration in this regard is the availability of D- and L-sugars, designated as such by the configuration of the chiral carbon most remote from the aldehydo/keto functionality (McNaught, A. D. *Pur. Appl. Chem.* 1996, 68, 1919-2008). L-sugars are often rare or unnatural products, but are known to have excellent potential as medicinal agents in their pyranosidic forms. For example, L-sugars are important constituents in antibiotics and other clinically useful agents such as heparin (*Heparin—Chemical and Biological Properties; Clinical Applications.* Lane, D. A.; Lindahl, U., eds. Edward Arnold: London, 1989). Known processes for making L-pyranosides include: (1) de novo syntheses (as illustrated in Ko, S. Y. et al. *Science* 1983, 220, 949-51), (2) homologation of shorter-chain sugars (as illustrated in Sowden, J. C. et al. *J. Am. Chem. Soc.* 1945, 67, 1713-15), and (3) epimerization of readily available D-sugars (as illustrated in Blanc-Muesser, M. et al, *Synthesis* 1977, 568-69). Methods for epimerizing D-sugars into L-sugars typically employ an acyclic intermediate to establish the L stereocenter, which often leads to a diastereomeric mixture of products upon cyclization. Several groups have reported epimerization of the critical stereocenter without opening the pyranose ring (as illustrated in Pegram, J. J.; et al., *Carbohydr. Res.* 1988, 184, 276-78); however, these routes have not demonstrated significant advantages in terms of synthetic efficiency or generality.

One method of synthesizing enantiopure THPs has been to transform common pyranosides such as D-glucose or D-galactose into DHPs known as D-glycals, in which the C1 and C2 substituents have been replaced with a double bond (enumerated positions used herein are based on the starting carbohydrate in accordance with standard nomenclature, see structure 1 below). Glycals have been widely used as synthetic intermediates in a variety of biologically active products, illustrating the value of such molecules (as illustrated in Tolstikov, A. G. et al., *Russ. Chem. Rev.* 1993, 62, 579). However, the D-glycal of structure 1 and related derivatives are limited in synthetic scope because certain substituents cannot be easily manipulated, particularly the C5 hydroxymethyl unit. This group defines the configuration of the carbohydrate (D or L) and is generally considered a permanent structural element on the ether ring. Moreover, access to L-glycals is severely limited by the poor availability of the corresponding L-sugars.

There is a continuing need for new and improved methods for synthesizing enantiopure DHPs and THPs from readily available chiral materials such as carbohydrates. In addition, there is a need for an efficient process for converting common D-pyranosides into natural or unnatural L-glycals and L-pyranosides without the aforementioned problems attendant to known techniques. 4-Deoxypentenosides (4-DPs), such as the compound of structure 2, are similar in appearance to glycals but possess a double bond on the other side of the pyranose ring. This structure, which was first reported in 1973 by Zemlicka and co-workers (Philips, K. D.; Zemlicka, J.; Horwitz, J. P. *Carbohydr. Res.* 1973, 30, 281-86), can be expected to have a similar reactivity profile to glycals with subsequent utility in organic synthesis. Compounds resulting from the synthetic application of 4-DPs and related DHPs are anticipated to be useful as medicinally active agents and other value-added products.

OBJECTS OF THE INVENTION

It is an object of the present invention to develop general methods and processes for synthesizing or making novel, enantiopure DHPs and THPs.

It is an additional object of the instant invention to provide novel, enantiopure intermediates which can be used to synthesize enantiopure THPs.

It is an additional object of the instant invention to provide novel processes for making enantiopure DHPs and THPs from common monosaccharides.

It is a still further object of the instant invention to provide an efficient and widely applicable process to convert common D-pyranosides through novel intermediates into natural and unnatural L-glycals and L-pyranosides.

It is yet a further object of the invention to provide compounds and compositions which may be made by the methods or using intermediates of the present invention.

Any one of these and/or other objects of the present invention may be readily gleaned from a description of the invention which follows.

SUMMARY OF THE INVENTION

Novel, enantiopure 4-deoxypentenosides (4-DPs) and related DHP intermediates are prepared from common carbohydrates via a novel process, and are used to prepare a wide variety of enantiopure tetrahydropyrans (THPs). The 4-DPs and related DHPs are amenable to a broad range of stereoselective transformations, including but not limited to: (i) formation of three-atom rings or transient intermediates; (ii) [n+2] cycloadditions with other π-systems, where n=2-6; (iii) electrophilic and nucleophilic additions to C4 and C5, including those mediated by organometallic species; and (iv) oxidative or reductive reactions, including those mediated by organometallic species such as hydrogenation, hydrometallation, or carbometallation.

Reactions of the instant invention include all synthetic reactions involving carbohydrate-derived 4-DPs and related DHPs as illustrated in Scheme 1 below, in which substituents $R_1$ through $R_3$ can be part of the native carbohydrate or installed by synthesis prior to the introduction of the C4-C5 double bond. For example, the invention provides a process to make novel 2-amino, 4-amino, and 2,4-diamino-THPs using 2-amino-4-deoxypentenosides derived from D-glucosamine ($R_1$=O, $R_2$=N, $R_3$=O). Substituents $R_1$-$R_3$ include but are not limited to groups containing: H, C(sp, sp$^2$, or sp$^3$) N, O, F, Si, P, S, Cl, Ge, Se, Br, Sn, Te, or I. Substituents X and Y include, but are not limited to groups containing: H, C(sp, sp$^2$, or sp$^3$), N, O, F, Si, P, S, Cl, Ge, Se, Br, Sn, Te, or I.

Scheme 1

Novel 4-DPs and related DHPs of the invention may be used as synthetic intermediates toward higher-order or exotic sugars and other complex THPs of commercial or medicinal value. In one embodiment of the instant invention, 4-DPs are converted to L-sugars in a novel process that offers at least the following distinct advantages over known synthetic methods. First, the process is a highly efficient approach which uses inexpensive reagents and common D-sugars as starting materials. Second, it provides a direct route to protected L-pyranosides with fixed anomeric configurations, and is directly adaptable to the construction of 1,4-linked saccharides such as the glycosaminoglycans. Third, it is an efficient method for the stereoselective installation of isotopic labels and is a particularly useful way to prepare 6-[$^{13}$C]-hexopyranosides. Fourth, the 4-DPs offer a novel route to higher-order sugars and complex intermediates for the construction of natural products with pyranosidic moieties.

As illustrated in Scheme 2 below, the instant invention provides a novel process for making enantiopure DHP intermediates of formula (I) with substituents $R_1$ through $R_3$ as defined above, by a tandem oxidation-decarboxylative elimination of 4,6-diols under reaction conditions described in detail hereinafter and exemplified in the General Synthetic Chemistry section of the Detailed Description of The Invention. As also illustrated in Scheme 2 below, the enantiopure DHP intermediates of formula (I) are oxidized by a novel process of the instant invention to yield novel 4,5-epoxypyranosides of formula (II) under reaction conditions described in detail hereinafter and exemplified in the General Synthetic Chemistry section of the Detailed Description of The Invention (e.g., Table 1).

Scheme 2

The novel 4,5-epoxypyranosides of formula (II) can be reacted with nucleophiles and undergo $S_N2$ ring opening at C5 to form THPs of formula (III) as shown in Scheme 3 below, where $R_1$-$R_3$ are as defined previously and Nu is a nucleophile which may include groups containing: H, C(sp, sp$_2$, or sp$_3$), N, O, F, Si, P, S, Cl, Ge, Se, Br, Sn, Te, or I. Some examples of specific nucleophiles include: Grignard reagents and other organometallic species derived from alkanes, alkenes, aromatic groups, and heterocycles; enolates and other α-stabilized carbanions; CN; heteroatomic nucleophiles such as $N_3$ and thiolates; hydrides. In this case, Nu has an anti relationship with the C4 substituent. The nucleophile may be neutral or charged, including neutral or anionic organometallic complexes (for example, a Grignard reagent combined with a cuprous salt).

Scheme 3

Epoxypyranosides of formula (II) can be reacted with nucleophiles under Lewis acid conditions to produce THPs of formula (IV) as shown in Scheme 4, where Nu and $R_1$-$R_3$ are as defined previously. In this case, the C5 stereochemistry is most likely determined by the formation of an early transition-state intermediate, such as an oxocarbenium ion, and is likely to produce an alternate diastereomeric relationship in which the C5 substituent has a syn relationship with the C4 substituent. This permits the efficient synthesis of pyranosides with L-ido configuration, which are important constituents in glycosaminoglycans such as heparin.

Scheme 4

Reaction Schemes 3 and 4 illustrate in an exemplary manner the wide range of stereoselective syntheses of enantiopure THPs that can be achieved in accordance with the instant invention. The stereochemistry illustrated in Schemes 3 and 4 is illustrative only; reaction conditions in Schemes 2, 3, and 4 can be varied to produce other stereoisomers at C4 and C5, such that each substituent at C1 through C5 may be disposed in α or β configuration (i.e., below or above the plane of the pyran moiety).

In accordance with Reaction Scheme 2 above, enantiopure 4-DPs and related DHPs of formula (I) are formed by oxidation-decarboxylative elimination of α-D-glucosides in an oxidizing reaction medium, comprising for example 2,2,6,6-tetra-methylpiperidinyloxy free radical (TEMPO) and an oxidant including, for example a hypochlorite/bromite solution comprising NaOCl, or NaOBr generated from NaOCl and KBr, an organic solvent, and water, followed by thermal decarboxylative elimination using dehydrative agent, for example dineopentyl N,N-dimethylformamide acetal in refluxing toluene. All inert organic solvents in principle should prove suitable for use in these reactions. Organic solvents which form a two-phase system with the aqueous solution are particularly preferred for the oxidative step. The reaction can also be carried out in a one-phase aqueous-organic solvent mixture. Particularly advantageous, however, are halogenated hydrocarbons such as, for example, dichloromethane, chloroform, 1,1,1-trichloroethane or else esters of formic acid and acetic acid.

Enantiopure 4-DPs and related DHP intermediates of formula (I) can be stereoselectively oxidized into epoxides, preferably by dimethyldioxirane (DMDO) in an organic solvent at low temperatures between about −75° C. and 0° C., to yield 4,5-epoxypyranosides of formula (II). Epoxide stereoselectivity is generally directed anti (to the face opposite) to two out of three substituents at C1, C2, and C3 when using achiral oxidants such as DMDO. Nucleophilic ring opening of the 4,5-epoxypyranosides of formula (II) can be effected by reacting them with carbon nucleophiles, for example Grignard reagents preferably at about −20° C. to about 0° C. (a broader range of temperatures may be applicable, for example as low as −50° C. to above room temperature, preferably at or below room temperature within this range) in the presence of a cuprous halide to produce novel THPs of formula (III) with inversion of stereochemistry at C5.

For example, in accordance with Reaction Scheme 2 above, enantiopure 4-DP intermediates of formula (I) are formed by oxidation-decarboxylative elimination of α-D-glucosides at around 0° C. in a reaction medium comprising in approximate amounts TEMPO (5 mol %), n-$Bu_4NBr$ (5 mol %), NaOCl, $NaHCO_3$, $CH_2Cl_2$ and water, followed by treatment with dineopentyl N,N-dimethylformamide acetal in refluxing toluene. Enantiopure 4-DP intermediates of formula (I) are oxidized with DMDO in dry acetone/$CH_2Cl_2$ at −55° C. to yield quantitatively 4,5-epoxypyranosides of formula (II) in a 10:1 β:α ratio.

As a further example, in accordance with Reaction Scheme 3 above, $S_N2$ ring openings of β-4,5-epoxypyranosides of formula (II) derived from α-D-glucosides are effected by reacting the 4,5-epoxypyranosides with Grignard reagents (3.5 equiv.) and CuI (10 mol %) at −20° C. to 0° C., in a reaction medium comprised of tetrahydrofuran (THF) or diethyl ether ($Et_2O$) to produce substituted THPs of formula (III) with anti C4 and C5 substituents in yields as high as 87%, in a 10:1 L-altro to D-gluco diastereomeric ratio.

In another example, in accordance with Reaction Scheme 4 above, Lewis-acid mediated ring openings of β-4,5-epoxypyranosides of formula (II) derived from α-D-glucosides are effected by reacting the 4,5-epoxypyranosides with a nucleophile (3 equiv.) and a Lewis acid such as $AlMe_3$ or $BF_3$ etherate (10 mol %) at −78° C., in a nonpolar reaction medium such as $CH_2Cl_2$ to produce substituted THPs of formula (IV) with syn C4 and C5 substituents in a 10:1 D-galacto to L-ido diastereomeric ratio.

Novel DHPs of the present invention also include compounds with β-anomeric (C1) substituents of formula (IV), where $R_1$ and $R_2$ are H, C (sp, $sp^2$, or $sp^3$), N, O, F, Si, P, S, Cl, Br, Se, Sn, Te, or I. These include L-glycals ($R_1$=C), which can be derived by the oxidation-decarboxylative elimination of β-C-glycosides. Novel 4,5-epoxypyranosides and THPs of the instant invention derived from DHPs of formula (V) include compounds of formula (VI) and formula (VII) respectively, where Nu is as described above and can be disposed in either the α or β configuration at C5 as described above. In this manner, the instant invention provides a generic and enantioselective route to novel DHPs of formula (I), novel 4,5-epoxypyranosides of formula (II), and novel THPs of formula (III).

V

In another aspect of the instant invention, protected L-pyranosides of formula (VIII) can undergo further functional group transformations to yield genuine L-hexopyranosides of structure (IX) in accordance with Scheme 5. In one example involving Tamao-Fleming oxidation of a C6 phenyldimethylsilyl (PDMS) group (Fleming, I.; Sanderson, P. E. J. *Tetrahedron Lett.* 1987, 28, 4229-32), the L-pyranoside is oxidized in $CH_3CO_3H$, KBr, AcOH, and NaOAc from 0° C. to around 40° C. to achieve a genuine L-altropyranoside in 75% yield.

Scheme 5

Compounds of the present invention may be used as intermediates in chemical synthesis, as biologically active agents such as pharmacological agents, antimicrobial agents (antibacterial, antiviral, insecticides, etc.), as food additives such as sweeteners, or as otherwise described herein. These novel compounds, and the novel processes of the instant invention, are described further in the following detailed description.

Compounds according to present invention may be exemplified by compounds of the formula:

wherein each substituent is disposed in an α or β configuration and where $R_1$ through $R_3$ are independently selected from H, a substituted or unsubstituted saturated or unsaturated hydrocarbon, a $NR^1R^2$ group, an $OR^2$ or alkylene $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, a carboxy or acyl group, azide, cyanide, thiocyanate or a halogen group with the proviso that $R_1$, $R_2$ and $R_3$ are not all simultaneously H;

$R^1$ and $R^2$ are independently selected from H, a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$R^3$ is H, a $C_1$-$C_{12}$ substituted or unsubstituted linear, branched or cyclic alkyl, alkenyl or alkynyl group, a substituted or unsubstituted aryl or heteroaryl group, an amino, alkyl amino or dialkyl amino group, an alkoxy or aryloxy group, or a carboxy or acyl group;

$R^4$ and $R^5$ are independently selected from H, $OR^6$, a $C_1$-$C_{12}$ substituted or unsubstituted linear, branched or cyclic alkyl, alkenyl or alkynyl group, a substituted or unsubstituted aryl or heteroaryl group, an acyl thioether or a halogen group; and

$R^6$ is selected from a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group.

The above compounds may be readily synthesized pursuant to the presentation of the scheme below. The following scheme represents the transformation of a typical monosaccharide into unsaturated 1,2-dihydropyranosides (glycals) or 2,3-dihydropyranosides, based on known reaction conditions (P represents typical functional groups used on carbohydrate derivatives, all of which have been described hereinabove. Groups $R_1$, $R_2$, and $R_3$ can be stereoselectively installed at their respective positions by functionalizing the double bond, again based upon known reaction conditions. These intermediates are deblocked and transformed by an efficient process described in the invention to yield 4-DPs and related DHPs.

General Chemical Scheme For
Chemical Synthons Made from Monosaccharides

Alternative chemical embodiments according to the present invention may be represented by the formulas:

where Bn is $CH_2C_6H_5$.

Alternative embodiments of compounds include those according to the structures:

wherein $R_1$, $R_2$ and $R_3$ are as described above;

X is O, S, SO, $NR^a$, $CR^aR^b$ or $SiR^cR^d$, where $R^a$ and $R^b$ are each independently H or a substituted or unsubstituted $C_1$-$C_6$ alkyl group, a substituted or unsubstituted aryl or heteroaryl group, and $R^c$ and $R^d$ are each independently H, a substituted or unsubstituted $C_1$-$C_6$ alkyl or alkenyl group, a substituted or unsubstituted aryl or heteroaryl group, a carboxy or acyl group, a halogen group, a trialkylsilyl group, or an $OR^e$ group where $R^e$ is a substituted or unsubstituted $C_1$-$C_6$ acyl, alkyl, alkenyl, or aryl group;

$X^1$ is obtained from X after nucleophilic addition and preferably is selected from the group consisting of OH, alkoxy, SH, thioether, thioester, sulfoxide, $HNR^a$, $HCR^aR^b$ and $HSiR^cR^d$, where $R^a$ and $R^b$ are each independently H or a substituted or unsubstituted $C_1$-$C_6$ alkyl group, an acyl or ester group group, a substituted or unsubstituted aryl or heteroaryl group and each of $R^c$ and $R^d$ is independently H, a substituted or unsubstituted $C_1$-$C_6$ alkyl group, a substituted or unsubstituted aryl or heteroaryl group, a halogen group or an $OR^e$ group, where $R^e$ is a $C_1$-$C_6$ alkyl group; and Nu is a group obtained after addition of a nucleophile to the compound containing X above, said Nu group being selected from H, substituted or unsubstituted alkyl, alkenyl, alkynyl, aryl, aralkyl or heteroaryl groups; nitrogen-containing groups including amino, mono- and disubstituted alkyl or aryl amino groups, azide, cyano, or thiocyanate; acyl groups (such as formyl, acetyl, and benzoyl); carboxyalkyl esters; oxygen-containing groups including hydroxy or alkoxy groups; halogens such as F, Cl, Br, and I; Si-containing groups including trialkylsilyl or alkylsiloxy groups; phosphorous-containing groups including phosphate, phosphinite, phosphonate or phosphoramidate groups; sulfur-containing groups including sulfite, sulfinite, sulfate, sulfonate or sulfonamide groups, thioethers, thiocyanate and thiocarbamates, Se- and Te-containing groups including SeH, Se-alkyl, Se-aryl, or Te-aryl; Sn-containing groups including trialkyltins.

DETAILED DESCRIPTION OF THE INVENTION

The terms below have the following definitions unless indicated otherwise. Other terms that are used to describe the present invention have the same definitions as those terms which are generally used by those skilled in the art.

The term "alkyl" is used herein to refer to a fully saturated monovalent hydrocarbon radical containing carbon and hydrogen, and which may be a straight chain, branched or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl. "Cycloalkyl" groups refer to cyclic alkyl groups such as cyclopropyl, cyclobutyl, cyclopentyl and cyclohexyl.

The term "substituted alkyl" refers to alkyl as just described which include one or more functional groups such as aryl, substituted aryl, acyl, alkylhalos (e.g., $CF_3$), halogen, hydroxy, alkoxy, alkoxyalkyl, amino, alkylamino, dialkylamino, acylamino, acyloxy, aryloxy, aryloxyalkyl, carboxyalkyl, carboxamido, thio, thioethers, both saturated and unsaturated cyclic hydrocarbons, heterocycles and the like. The term "substituted cycloalkyl" has essentially the same definition as and is subsumed under the term "substituted alkyl" for purposes of describing the present invention. In other instances where the term "substituted" is used, the substituents which fall under this definition may be readily gleaned from the other definitions of substituents which are presented in the specification as well the circumstances or context under which such substituents occur in a given chemical compound.

The term "aryl" refers to a substituted or unsubstituted monovalent aromatic radical having a single ring (e.g., phenyl) or multiple condensed rings (e.g., naphthyl). Other examples include heterocyclic aromatic ring groups (heteroaryls) having one or more nitrogen, oxygen, or sulfur atoms in the ring, such as imidazolyl, furyl, pyrrolyl, pyridyl, thienyl and indolyl, among others.

The term "substituted aryl" refers to an aryl as just described that contains one or more functional groups such as lower alkyl, acyl, aryl, halogen, alkylhalos (e.g., $CF_3$), hydroxyl, alkoxyl, alkoxyalkyl, amino, alkylamino, dialkylamino, acylamino, acyloxy, aryloxy, aryloxyalkyl, carboxyalkyl, carboxamido, thio, thioethers, both saturated and unsaturated cyclic hydrocarbons, heterocycles and the like. A substituted aryl also describes an alkylene aryl group such as a benzyl or a related group.

The term "Elimination agent" refers to a chemical agent useful in the removal of one or more functional groups by elimination, resulting in or producing an unsaturated double bond. Elimination agents useful in the processes of the instant invention include formamide acetals and other orthoamides, orthoesters, acid chlorides, activated carbonyls and carbonates, thionyl chloride and activated sulfites, sulfates, sulfonates, and sulfuranes, activated phosphites, phosphonates, and phosphates, selenium and tellurium reagents, and the like.

The term "Functionalized pyranosides" or more simply, "functionalized" refers to tetrahydropyrans which have been functionalized at one or more positions on the ring carbons (e.g., C1, C2, etc.) or preexisting functional groups (e.g., O1, N2, etc.), derived from carbohydrates such as glucose, mannose, galactose, xylose, arabinose, ribose, fructose, fucose, rhamnose, and the like.

"Heterocycle" or "heterocyclic" refers to a carbocylic ring wherein one or more carbon atoms have been replaced with one or more heteroatoms such as nitrogen, oxygen or sulfur. Examples of heterocycles include, but are not limited to, piperidine, pyrrolidine, morpholine, thiomorpholine, piperazine, tetrahydrofuran, dihydropyran (DHP), tetrahydropyran (THP), 2-pyrrolidinone, δ-valerolactam, δ-valerolactone and 2-ketopiperazine, among numerous others, including heteroaryls. The term "substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. Substituted heterocycles include alkylene heterocycle groups.

The term "effective amount" refers to the amount of a selected compound, intermediate or reactant which is used to produce an intended result. The precise amount of a compound, intermediate or reactant used will vary depending upon the particular compound selected and its intended use, the synthetic methods employed, and, in the case of pharmaceutical compounds, the age and weight of the subject, route of administration, and so forth, but may be easily determined by routine experimentation. In the case of the treatment of a condition or disease state, an effective amount is that amount which is used to effectively treat the particular condition or disease state.

The term "enantiomers" refers to two stereoisomers of a compound which are non-superimposable mirror images of one another. "Stereoisomers" refers to compounds which have identical chemical constitution, but differ with regard to the arrangement of their atoms or groups in space. A "stereoselective process" is one which favors production of one particular stereoisomer as a reaction product. "Enantiopure" or "enantomerically pure" means a pure stereoisomer uncontaminated by its enantiomer. "Enantiomerically enriched" means a compounds in which one of two (or more) enantiomers is found in greater concentrations in a given sample than another enantiomer. "Quantitative yields" refers to the complete chemical conversion of a reactant to a product. "Facioselectivity" refers to the strong preference of a chemical reagent to add across either the α or β face of a reaction intermediate.

The term "dioxirane" is art-recognized and refers to a three-membered ring which consists of two oxygen atoms and one carbon atom, wherein the carbon atom bears two substituents that render it tetrahedral. "DMDO" refers to dimethyl dioxirane.

"Lewis acid" means any species that can coordinate with a lone pair of electrons from a conjugate base. Lewis acids useful in processes of the instant invention include but are not limited to alkali and alkali-earth metal ions such as Li, Be, Na, Mg, K, and Ca, $BF_3$ etherate, $EtAlCl_2$, $SiCl_4$, $MeSi_3$, $PCl_5$, and the like. The Lewis acid may be cationic or a coordinatively unsaturated transition-metal or main-group compound (e.g., Li salts, $BF_3$ etherate, etc.).

"Oxidizing reaction medium" refers to a reaction medium comprising a stoichiometric oxidant species, whose electron transfer is sometimes facilitated by a reduction-oxidation catalyst. Examples of compounds which can be employed as catalysts are organic species such as 2,2,6,6-tetramethyl-1-piperidinyloxy (TEMPO), 4-phenyl-2,2,5,5-tetramethyl-3-imidazolin-1-yloxy-3-oxide, 3-(aminomethyl)-2,2,5,5-tetramethyl-N-pyrrolidinyloxy, 3-carbamoyl-2,2,5,5-tetramethyl-N-pyrrolidinyloxy; transition-metal salts such as iron, chromium, manganese; main-group elements such as boranes, aluminum(III) species, and the like. "Oxidants" include halogens, high-oxidation state halides such as hypochlorite, chlorite; hypobromite, bromite, bromate; hypoiodite, iodite, iodate, and periodate; activated sulfonium species, peroxides and peroxy acids, persulfate, permanganate and related high-oxidation state main-group and transition metal ions, and the like.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions. Illustrative anionic nucleophiles include simple anions such as azide, cyanide, thiocyanate, acetate, formate or chloroformate, and bisulfite. Organometallic reagents such as organocuprates, organozincs, organolithiums, Grignard reagents, enolates, acetylides, and the like are also suitable nucleophiles. Hydride may also be a suitable nucleophile when reduction of the substrate is desired.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Based on the IUPAC Nomenclature of Carbohydrates (1996 Recommendations), which is incorporated herein by reference, the following carbohydrate terminology is used herein "Parent monosaccharides" are polyhydroxy aldehydes H—[CHOH]$_n$—CHO or polyhydroxy ketones H—[CHOH]$_n$—CO—[CHOH]$_m$—H with three or more carbon atoms.

The generic term "monosaccharide" (as opposed to oligosaccharide or polysaccharide) denotes a single unit, without glycosidic connection to other such units. It includes aldoses, dialdoses, aldoketoses, ketoses and diketoses, as well as deoxy sugars and amino sugars, and their derivatives, provided that the parent compound has a (potential) carbonyl group.

Monosaccharides with an aldehydic carbonyl or potential aldehydic carbonyl group are called "aldoses"; those with a ketonic carbonyl or potential ketonic carbonyl group, "ketoses". The term 'potential aldehydic carbonyl group' refers to the hemiacetal group arising from ring closure. Likewise, the term 'potential ketonic carbonyl group' refers to the corresponding hemiketal structure.

Cyclic hemiacetals or hemiketals of sugars with a five-membered (tetrahydrofuran) ring are called "furanoses", those with a six-membered (tetrahydropyran) ring "pyranoses".

Monosaccharides containing two (potential) aldehydic carbonyl groups are called "dialdoses".

Monosaccharides containing two (potential) ketonic carbonyl groups are termed "diketoses".

Monosaccharides containing a (potential) aldehydic group and a (potential) ketonic group are called "ketoaldoses".

Monosaccharides in which an alcoholic hydroxy group has been replaced by a hydrogen atom are called "deoxy sugars".

Monosaccharides in which an alcoholic hydroxy group has been replaced by an amino group are called "amino sugars". When the hemiacetal hydroxy group is replaced, the compounds are called glycosylamines.

"Glycosides" are mixed acetals formally arising by elimination of water between the hemiacetal or hemiketal hydroxy group of a sugar and a hydroxy group of a second compound. The bond between the two components is called a glycosidic bond.

"Oligosaccharides" are compounds in which monosaccharide units are joined by glycosidic linkages. According to the number of units, they are called disaccharides, trisaccharides, tetrasaccharides, pentasaccharides etc. The borderline with polysaccharides cannot be drawn strictly; however the term 'oligosaccharide' is commonly used to refer to a defined structure as opposed to a polymer of unspecified length or a homologous mixture. When the linkages are of other types, the compounds are regarded as oligosaccharide analogues.

"Polysaccharide" (glycan) is the name given to a macromolecule consisting of a large number of monosaccharide (glycose) residues joined to each other by glycosidic linkages. The term poly(glycose) is not a full synonym for polysaccharide (glycan), because it includes macromolecules composed of glycose residues joined to each other by non-glycosidic linkages.

For polysaccharides containing a substantial proportion of amino sugar residues, the term polysaccharide is adequate, although the term glycosaminoglycan may be used where particular emphasis is desired. Polysaccharides composed of only one kind of monosaccharide are described as "homopolysaccharides (homoglycans)". Similarly, if two or more different kinds of monomeric unit are present, the class name heteropolysaccharide (heteroglycan) may be used.

The term "glycan" has also been used for the saccharide component of a glycoprotein, even though the chain length may not be large.

The term polysaccharide has also been widely used for macromolecules containing glycose or alditol residues in which both glycosidic and phosphate diester linkages are present.

Conventions

Names of examples are given with an initial capital letter (e.g. 'L-glycero-β-D-gluco-Heptopyranose') to clarify the usage in headings and to show which letter controls the ordering in an alphabetical index.

The following abbreviations are commonly used for substituent groups in structural formulae: Ac (acetyl), Bn or PhCH$_2$ (benzyl), Bz or PhCO (benzoyl), Et (ethyl), Me (methyl), Me$_3$Si (not TMS) (trimethylsilyl), Bu$^t$Me$_2$Si (not TBDMS) (tert-butyldimethylsilyl), Ph (phenyl), Tf (triflyl=trifluoromethanesulfonyl), Ts (tosyl=toluene-p-sulfonyl), Tr (trityl).

A new center of chirality generated by hemiacetal ring closure is called the "anomeric center"; the related two stereoisomers are referred to as anomers, designated α or β according to the configurational relationship between the anomeric center and a specified anomeric reference atom.

The anomeric reference atom is the configurational atom of the parent, unless multiple configurational prefixes are used. If multiple configurational prefixes are used, the anomeric reference atom is the highest-numbered atom of the group of chiral centers next to the anomeric center that is involved in the heterocyclic ring and specified by a single configurational prefix. In the α anomer, the exocyclic oxygen atom at the anomeric center is formally cis, in the Fischer projection, to the oxygen attached to the anomeric reference atom; in the β anomer these oxygen atoms are formally trans.

The anomeric symbol α or β, followed by a hyphen, is placed immediately before the configurational symbol D or L of the trivial name or of the configurational prefix denoting the group of chiral carbon atoms that includes the anomeric reference atom.

EXAMPLES

α-D-gluco
α-D-Glucopyranose TOP carbon is anomeric

β-D-gluco
β-D-Glucopyranose TOP carbon is anomeric

α-L-arabino
Methyl α-L-arabinopyranoside TOP carbon is anomeric

L-glycero-α-D-manno
Methyl L-glycero-α-D-manno-heptopyranoside TOP carbon is anomeric D-glycero-β-D-galacto TOP carbon is anomeric
Methyl 5-acetamido-3,5-dideoxy-D-glycero-β-D-galacto-non-2-ulopyranosonate ⟶ denotes the anomeric reference atom TOP carbon is anomeric;
⟹ denotes the configurational atom.

For simple aldoses up to aldohexoses, and ketoses up to hept-2-uloses, the anomeric reference atom and the configurational atom are the same.

The conformational symbols for enantiomers are different. It is therefore important to state in the context whether the D or the L form is under consideration. Enantiomers have the same reference plane, and it should be noted that the mirror image of α-D-glucose-$^4C_1$ is α-L-glucose-$^1C_4$.

Mirror images: α-D-glucopyranose-$^4C_1$ (upper) and α-L-glucopyranose-$^1C_4$ (lower)

For six-membered rings, the following terms may be used.

"Chairs": The reference plane is defined by two parallel ring sides, so chosen that the lowest-numbered carbon atom in the ring is exoplanar.

"Boats": The reference plane is defined by the two parallel 'sides' of the boat.

"Skews": Each skew form has two potential reference planes, containing three adjacent atoms and the remaining non-adjacent atom. The reference plane is so chosen that the lowest-numbered carbon atom in the ring, or the atom numbered next above it, is exoplanar, in that order of preference.

"Half-chairs": The reference plane is defined by the four adjacent coplanar atoms.

"Envelopes": The reference plane is defined by the five adjacent coplanar atoms.

The term "reaction product" means a compound which results from the reaction of the two substrate molecules. In general, the term "reaction product" will be used herein to refer to a stable, isolable compound, and not to unstable intermediates or transition states.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the instant invention which are basic in nature are capable of forming a wide variety of different pharmaceutically-acceptable salts with various inorganic and organic acids. Although such salts must be pharmaceutically acceptable for administration to animals, it is often desirable in practice to initially isolate a compound of the instant invention from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methane-sulfonate and pamoate [i.e., 1,1'-methylene-bis-(2-hydroxy-3-naphthoate)] salts.

Those compounds of the instant invention which are also acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of the instant invention. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

General Synthetic Chemistry

All reactions discussed hereinafter proceed at atmospheric pressure unless otherwise noted. In accordance with Reaction Scheme 6 below, 4-DPs 2a-f were prepared from their corresponding α-D-glucosides in 60-80% isolated yield by a tandem oxidation-decarboxylative elimination. The reaction conditions were as follows: (i) TEMPO (5 mol %), $Et_4NBr$ (5 mol %), 3:3:4 5% aq NaOCl:aq satd $NaHCO_3$:$CH_2Cl_2$, 0° C.; (ii) dineopentyl N,N-dimethylformamide acetal (5 equiv), toluene, 120° C. or xylenes, 150° C.

Scheme 6

Epoxypyranosides 3a-f were obtained from 4-DPs 2a-f by stereoselective reaction with DMDO at low temperatures, which proceeded quantitatively with facioselectivity varying as a function of substituents at C1, C2, and C3 as determined by $^1H$ NMR spectroscopy (300 MHz, $C_6D_6$). For example, epimerization at C1 or C2 to β resulted in high selectivity for epoxidation of the α face (see Table 1). In all instances, selectivities for α vs. β epoxidation were directed anti to two out of the three substituents at C1-C3. This may be due to the influence of the transannular substituents on the DHP ring conformation as well as the local steric environment.

TABLE 1

Stereoselective epoxidation of 2a-f

| Comp. | $R_1$ | $R_2$ | epoxide stereoselectivity (α:β) |
|---|---|---|---|
| 2a | OMe (α) | OBn (α) | 1:10[a] |
| 2b | OMe (α) | OBn (β) | 20:1[b] |
| 2c | OiPr (β) | OBn (α) | 5:1[b] |
| 2d | $CH_2OBn$ (β) | OH (α) | 10:1[a] |
| 2e | $CH_2PDMS$ (β) | OH (α) | 9:1[a] |
| 2f | OMe (β) | NPhth (α) | 8:1[a] |

[a]DMDO (0.1 M), acetone-$CH_2Cl_2$, −55° C.
[b]DMDO (0.1 M), acetone-$CH_2Cl_2$, 0° C.

Figure 1:
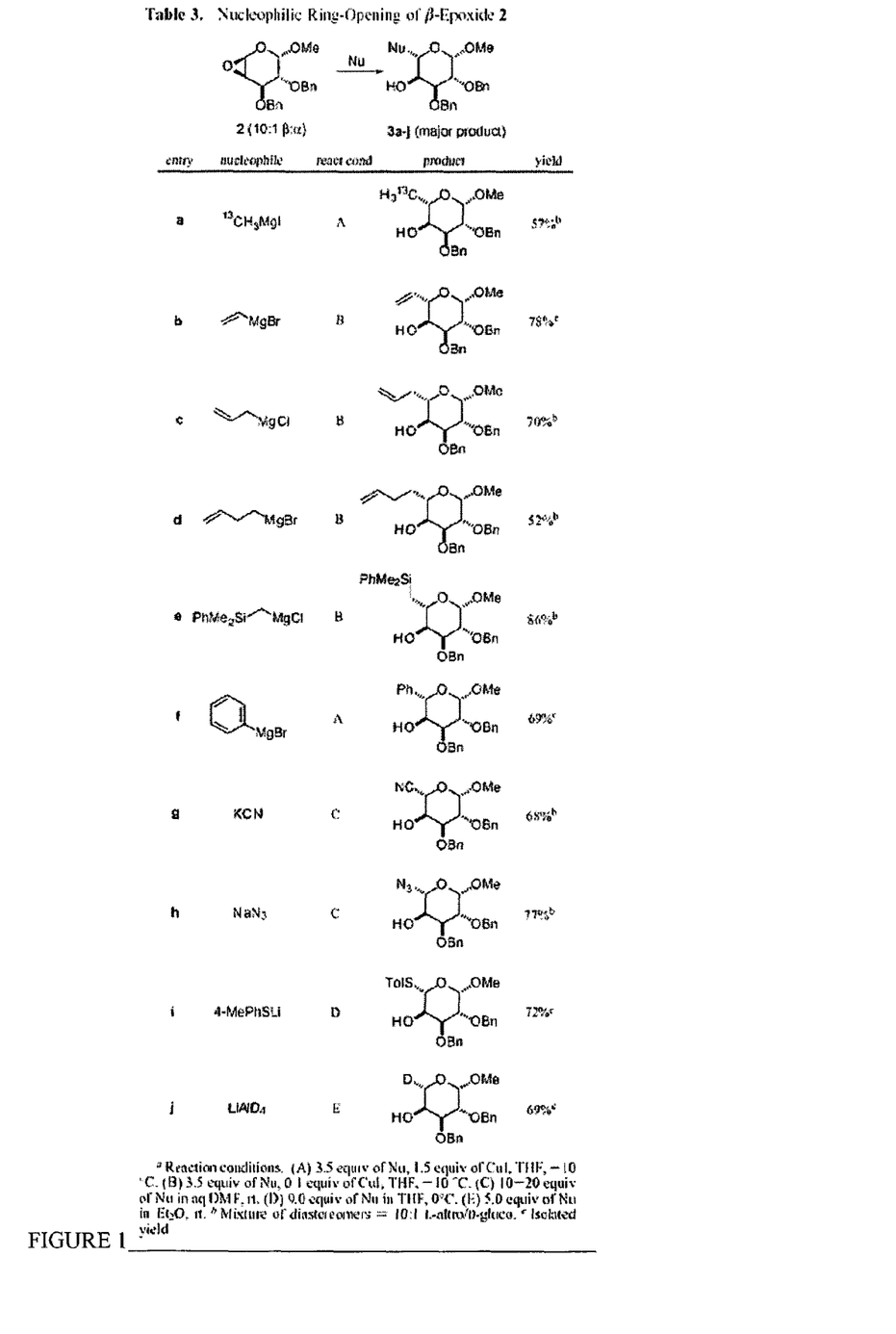
FIG. 1, in Table 3, lists representative L-pyranosides obtained by reacting novel 4,5-epoxypyranosides with carbon and heteroatom nucleophiles in accordance with the invention.

Epoxypyranosides 3a-f are stable in a range of solvents and at elevated temperatures. Several of these have been evaluated for their reactivity with nucleophiles under $S_N2$ and Lewis-acid mediated conditions. Ring-opening of β-epoxide 3a by anionic nucleophiles proceeds with complete regioselectivity and inversion of stereochemistry at C5, producing the corresponding L-altro derivatives in good to excellent yields in accordance with Reaction Scheme 3. In particular, Cu(I)-assisted Grignard additions proceed with both high yields and stereocontrol. It is interesting to note that the high levels of inversion of configuration observed here are better in some cases than the corresponding nucleophilic additions to α-epoxy glycals and related intermediates. Additions to the minor α-epoxide accompanying 3a also proceed with inversion at C5 to yield the corresponding D-gluco derivatives. Coupling constant analysis indicates that both epoxide isomers are predisposed to 1,2-diaxial ring opening at C5; in the case of the α-epoxide, the opposite half-chair is favored with O2 and O3 pseudoaxial configurations. Heteroatomic nucleophiles also add in an $S_N2$ fashion, yielding novel 1,5-bisacetals. The Table in FIG. 1 lists the conditions of various nucleophilic additions to 3a and their conversions into the corresponding L-altro derivatives in accordance with the invention.

What is claimed is:

1. An enantiopure compound according to the formula:

wherein each substituent $R_1$, $R_2$ and $R_3$ is disposed in an α or β configuration and where $R_1$ is selected from a $NR^1R^2$ group, an $OR^2$ group other than OAc or $OCH_3$, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, azide, cyanide, thiocyanate or a halogen group;

$R_2$ and $R_3$ are independently selected from H, a substituted or unsubstituted saturated or unsaturated hydrocarbon, a $NR^1R^2$ group, an $OR^2$ or alkylene $OR^2$ group other than OAc or $OCH_3$, a $SiR^3R^4R^5$ group, a $PR^4R^5$ group, a $P(O)R^4R^5$ or $P(O^2)R^4R^5$ group, a $SR^3$ group, a $S(O)R^4$ or $S(O_2)R^4$ group, a carboxy or acyl group, azide, cyanide, thiocyanate or a halogen group, with the proviso that $R_1$, $R_2$ and $R_3$ are not all simultaneously H;

$R^1$ and $R^2$ are independently selected from H, a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$R^3$ is H, a $C_1$-$C_{12}$ substituted or unsubstituted linear, branched or cyclic alkyl, alkenyl or alkynyl group, a substituted or unsubstituted aryl or heteroaryl group, an amino, alkyl amino or dialkyl amino group, an alkoxy or aryloxy group, or a carboxy or acyl group;

$R^4$ and $R^5$ are independently selected from H, $OR^6$, a $C_1$-$C_{12}$ substituted or unsubstituted linear, branched or cyclic alkyl, alkenyl or alkynyl group, a substituted or unsubstituted aryl or heteroaryl group, an acyl thioether or a halogen group; and $R^6$ is selected from a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group.

2. A compound of claim 1 of the formula:

where Bn is $CH_2C_6H_5$.

3. A compound of claim 2, wherein $R_1$ is a O-containing substituent other than OAc or $OCH_3$.

4. A compound of claim 2, wherein $R_2$ is a N- or O-containing substituent other than OAc or $OCH_3$.

5. A compound of claim 2, wherein $R_1$ and $R_2$ are $NR^1R^2$ or $OR^2$ where $R^1$ is H or an alkyl group and $R_2$ is an unsubstituted or substituted alkyl group, aryl group, acyl group or heteroaryl group other than Ac, Bn or $CH_3$.

6. A compound of claim 1 of the formula:

where Bn is $CH_2C_6H_5$.

7. A compound of claim 1 of the formula:

where Bn is $CH_2C_6H_5$.

8. A compound of claim 1 of the formula:

wherein $R^1$ is H or a $C_1$-$C_{12}$ alkyl group and $R^{2a}$ is a $C_1$-$C_{12}$ alkyl group or $NR^1R^{2a}$ form an azide group or an amide group where $R^1$ is H and $R^2$ is an acyl group containing a $C_1$-$C_{12}$ alkyl group and $OR^2$ is a group other than OAc or $OCH_3$; and Bn is $CH_2C_6H_5$.

9. An enantiopure compound according to the formula:

wherein each substituent $R_1$, $R_2$ and $R_3$ is disposed in an α or β configuration and where $R_1$ is selected from a $NR^1R^2$ group, an $OR^2$, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, azide, cyanide, thiocyanate or a halogen group;

$R_2$ and $R_3$ are each independently selected from H, a substituted or unsubstituted saturated or unsaturated hydrocarbon, a $NR^1R^2$ group, an $OR^2$ or alkylene $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, a carboxy or acyl group, azide, cyanide, thiocyanate or a halogen group, with the proviso that $R_1$, $R_2$ and $R_3$ are not all simultaneously H;

$R^1$ and $R^2$ are independently selected from H, a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$R^3$ is H, a $C_1$-$C_{12}$ substituted or unsubstituted linear, branched or cyclic alkyl, alkenyl or alkynyl group, a substituted or unsubstituted aryl or heteroaryl group, an amino, alkyl amino or dialkyl amino group, an alkoxy or aryloxy group, or a carboxy or acyl group;

$R^4$ and $R^5$ are independently selected from H, $OR^6$, a $C_1$-$C_{12}$ substituted or unsubstituted linear, branched or cyclic alkyl, alkenyl or alkynyl group, a substituted or unsubstituted aryl or heteroaryl group, an acyl thioether or a halogen group; and $R^6$ is selected from a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group; and

X is O, S, SO, $NR^a$, $CR^aR^b$ or $SiR^cR^d$, where $R^a$ and $R^b$ are each independently H or a substituted or unsubstituted $C_1$-$C_6$ alkyl group, a substituted or unsubstituted aryl or heteroaryl group, and $R^c$ and $R^d$ are each independently H, a substituted or unsubstituted $C_1$-$C_6$ alkyl or alkenyl group, a substituted or unsubstituted aryl or heteroaryl group, a carboxy or acyl group, a halogen group, a trialkylsilyl group, or an $OR^e$ group where $R^e$ is a substituted or unsubstituted $C_1$-$C_6$ acyl, alkyl, alkenyl, or aryl group.

10. A compound of claim 9 of the formula:

where Bn is $CH_2C_6H_5$.

11. A compound of claim 9 of the formula:

where Bn is $CH_2C_6H_5$.

12. A compound of claim 9 of the formula:

where Bn is $CH_2C_6H_5$.

13. An enantiopure compound according to the formula:

obtained from the reaction of a nucleophilic group with the compound of claim 10 wherein each substituent $R_1$, $R_2$ and $R_3$ is disposed in an α or β configuration and where $R_1$ is selected from a $NR^1R^2$ group, an $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, azide, cyanide, thiocyanate or a halogen group;

$R_2$ and $R_3$ are each independently selected from H, a substituted or unsubstituted saturated or unsaturated hydrocarbon, a $NR^1R^2$ group, an $OR^2$ or alkylene $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, a carboxy or acyl group, azide, cyanide, thiocyanate or a halogen group with the proviso that $R_1$, $R_2$ and $R_3$ are not all simultaneously H;

$R^1$ and $R^2$ are independently selected from H, a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$R^3$ is H, a $C_1$-$C_{12}$ substituted or unsubstituted linear, branched or cyclic alkyl, alkenyl or alkynyl group, a substituted or unsubstituted aryl or heteroaryl group, an amino, alkyl amino or dialkyl amino group, an alkoxy or aryloxy group, or a carboxy or acyl group;

$R^4$ and $R^5$ are independently selected from H, $OR^6$, a $C_1$-$C_{12}$ substituted or unsubstituted linear, branched or cyclic alkyl, alkenyl or alkynyl group, a substituted or unsubstituted aryl or heteroaryl group, an acyl thioether or a halogen group; and R⁶ is selected from a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$X^1$ is obtained from X after nucleophilic addition and is selected from the group consisting of OH, alkoxy, SH, thioether, thioester, sulfoxide, $HNR^a$, $HCR^aR^b$ and $HSiR^cR^d$, where $R^a$ and $R^b$ are each independently H or a substituted or unsubstituted $C_1$-$C_6$ alkyl group, an acyl or ester group, a substituted or unsubstituted aryl or heteroaryl group and each of $R^c$ and $R^d$ is independently H, a substituted or unsubstituted $C_1$-$C_6$ alkyl group, a substituted or unsubstituted aryl or heteroaryl group, a halogen group or an $OR^e$ group, where $R^e$ is a $C_1$-$C_6$ alkyl group; and

Nu is a group obtained after addition of a nucleophile to the compound containing X in claim 10, said Nu group being selected from H, substituted or unsubstituted alkyl, alkenyl, alkynyl, aryl, aralkyl or heteroaryl groups; amino, mono- and disubstituted alkyl or aryl amino groups, azide, cyano, or thiocyanate; acyl groups; carboxyalkyl esters; hydroxy or alkoxy groups; halogens trialkylsilyl or alkylsiloxy groups; phosphate, phosphinite, phosphonate or phosphoramidate groups; sulfite, sulfinite, sulfate, sulfonate or sulfonamide groups, thioethers, thiocyanate or thiocarbamates, SeH, Se-alkyl, Se-aryl, or Te-aryl groups; and trialkyltins.

14. A compound of claim 13 of the formula:

wherein Bn is $CH_2C_6H_5$.

15. A compound of claim 13 of the formula:

wherein Bn is $CH_2C_6H_5$.

16. A compound of claim 13 of the formula:

wherein Bn is $CH_2C_6H_5$.

17. A process for synthesizing enantiopure, substituted tetrahydropyrans comprising:
(a) synthesizing enantiopure 4-deoxypentenosides and structurally related 4,5-dihydropyrans by (i) tandem oxidation-decarboxylative elimination of pyranoside 4,6-diol compounds, achieved by reacting said pyranosides compounds in a reaction medium comprising an oxidizing reaction medium, an organic solvent, and water at a reaction temperature of about −10° C. to around 10° C. to form a reactant, and (ii) treatment of the reactant with an elimination agent in hot organic solvent;
(b) epoxidation of enantiopure 4-deoxypentenosides and structurally related 4,5-dihydropyrans with dioxiranes in a dry organic solvent between about −75° C. and about 0° C. to yield 4,5-epoxypyranosides with high facioselectivity; and
(c) nucleophilic ring opening of the 4,5-epoxypyranosides under either (i) $S_N2$ conditions using anionic nucleophiles with inversion of configuration at C5, in a reaction medium comprising one or more organic solvents, or (ii) Lewis-acid mediated conditions using anionic or neutral nucleophiles as low as −78° C. in a reaction medium comprising nonpolar organic solvents and a Lewis acid catalyst.

18. A process for making enantiopure, substituted tetrahydropyrans from a carbohydrate-derived monosaccharides comprising:
(a) synthesizing enantiopure 4-deoxypentenosides and structurally related 4,5-dihydropyrans by (i) oxidation of the monosaccharide at about −10 to 0° C. in a reaction medium comprising between about 5 and 10% 2,2,6,6-tetramethylpiperdinyloxy free radical (TEMPO) on a molar basis, between 5 and 10% n-$Bu_4$NBr on a molar basis, effective amounts of NaOCl, $NaHCO_3$, $CH_2Cl_2$, and water, and (ii) treating the reactant with dineopentyl N,N-dimethylformamide acetal in refluxing solvent (e.g. toluene);
(b) epoxidation of enantiopure 4-deoxypentenosides and structurally related 4,5-dihydropyrans with dimethyldioxirane (DMIDO) in acetone and $CH_2Cl_2$ between −75 and 0° C. to obtain 4,5-epoxypyranosides in quantitative yields with high levels of facioselectivity; and (c) effecting nucleophilic ring opening of the 4,5-epoxypyranosides by either (i) nucleophilic addition in a reaction medium comprising of THF or $Et_2O$ between about −40 and 0° C. with inversion of configuration at C5, or (ii) subjecting the 4,5-epoxypyranosides to Lewis-acid assisted nucleophilic ring opening in a reaction medium comprising a nonpolar solvent such as $CH_2Cl_2$ or toluene at about −78° C. to 0° C.

19. The process of claim 18, wherein the nucleophile is a neutral or anionic organometallic species, and the Lewis acid is a cationic or a coordinatively unsaturated transition-metal or main-group compound.

20. A process for making enantiopure 4,5-epoxypyranosides by reacting dimethyldioxirane (DMDO) in an organic solvent between −75° C. and 0° C. with substituted dihydropyranosides of the formula:

wherein each of $R_1$, $R_2$, $R_3$, are disposed in an α or β configuration, $R_1$ is selected from a $NR^1R^2$ group, an $OR^2$ group, a $SiR^3R^4R^5$ group, a $PR^4R^5$ group, a P(O)

$R^4R^5$ or $P(O_2)R^4R^5$ group, a $SR^3$ group, a $S(O)R^4$ or $S(O_2)R^4$ group, azide, cyanide, thiocyanate or a halogen group;

$R_2$ and $R_3$ are independently selected from H, a substituted or unsubstituted saturated or unsaturated hydrocarbon, a $NR^1R^2$ group, an $OR^2$ or alkylene $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, a carboxy or acyl group, azide, cyanide, thiocyanate or a halogen group with the proviso that $R_1$, $R_2$ and $R_3$ are not all simultaneously H;

$R^1$ and $R^2$ are independently selected from H, a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$R^3$ is H, a $C_1$-$C_{12}$ substituted or unsubstituted linear, branched or cyclic alkyl, alkenyl or alkynyl group, a substituted or unsubstituted aryl or heteroaryl group, an amino, alkyl amino or dialkyl amino group, an ailcoxy or aryloxy group, or a carboxy or acyl group;

$R^4$ and $R^5$ are independently selected from H, $OR^6$, a $C_1$-$C_{12}$ substituted or unsubstituted linear, branched or cyclic alkyl, alkenyl or alkynyl group, a substituted or unsubstituted aryl or heteroaryl group, an acyl thioether or a halogen group; and $R^6$ is selected from a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a tnalkylsilyl group, a phosphate, phosphinite, phosphonate or phosphoramidate group, or a sulfite, sulfinite, sulfate, sulfonate or sulfonamide group.

21. A process for making enantiopure, substituted tetrahydropyrans with L configuration at $C_5$ by reacting carbon nucleophiles at around −20° C. to 0° C. in a reaction medium comprised of one or more polar organic solvents, a cuprous halide, and 4,5-epoxypyranosides of the formula:

wherein each of $R_1$, $R_2$, $R_3$, are disposed in an α or β configuration, $R_1$ is selected from a $NR^1R^2$ group, an $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, azide, cyanide, thiocyanate or a halogen group;

$R^2$ and $R^3$ are independently selected from H, a substituted or unsubstituted saturated or unsaturated hydrocarbon, a $NR^4R^2$ group, an $OR^2$ or alkylene $OR^2$ group, a $SiR^3R^4R^5$ group, a $PR^4R^5$ group, a $P(O)R^4R^5$ or $P(O_2)R^4R^5$ group, a $SR^3$ group, a $S(O)R^4$ or $S(O_2)R^4$ group, a carboxy or acyl group, azide, cyanide, thiocyanate or a halogen group with the proviso that $R_1$, $R_2$ and $R_3$ are not all simultaneously H;

$R^1$ and $R^2$ are independently selected from H, a $C_1$-$C_{12}$ substituted or unsubstituted linear, branched or cyclic alkyl, aikenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group;

$R^3$ is H, a $C_1$-$C_{12}$ substituted or unsubstituted linear, branched or cyclic alkyl, alkenyl or alkynyl group, a substituted or unsubstituted aryl or heteroaryl group, an amino, alkyl amino or dialkyl amino group, an alkoxy or aryloxy group, or a carboxy or acyl group;

$R^4$ and $R^5$ are independently selected from H, $OR^6$, a $C_1$-$C_{12}$ substituted or unsubstituted linear, branched or cyclic alkyl, alkenyl or alkynyl group, a substituted or unsubstituted aryl or heteroaryl group, an acyl thioether or a halogen group; and $R^6$ is selected from a $C_1$-$C_{12}$ substituted or unsubstituted linear, branched or cyclic alkyl, alkenyl or alkynyl group, a substituted or unsubstituted aryl or heteroaryl group, a carboxy, acyl, or imidate group, a trialkylsilyl group, a phosphate, phosphinite, phosphonate or phosphoramidate group, or a sulfite, sulfinite, sulfate, sulfonate or sulfonamide group.

22. A composition comprising a pharmaceutically acceptable carrier and a therapeutically effective amount of a compound derived from intermediates produced by claim 20, or a pharmaceutically acceptable salt or thereof.

23. A composition comprising a pharmaceutically acceptable carrier and a therapeutically effective amount of a compound derived from intermediates produced by claim 21, or a pharmaceutically acceptable salt or thereof.

24. A composition comprising a pharmaceutically acceptable carrier and a therapeutically effective amount of a compound derived from intermediates produced by claim 19, or a pharmaceutically acceptable salt or thereof.

\* \* \* \* \*